United States Patent
Ruokonen (10) Patent No.: US 10,856,779 B2
(45) Date of Patent: Dec. 8, 2020

(54) APPARATUS, METHOD AND SOFTWARE APPLICATION FOR PHYSICAL COACHING

(71) Applicant: Sorvi Consulting Oy, Helsinki (FI)

(72) Inventor: Arto Ruokonen, Helsinki (FI)

(73) Assignee: SORVI CONSULTING OY

( * ) Notice: Subject to any disclaimer, the term of this patent is extended or adjusted under 35 U.S.C. 154(b) by 0 days.

(21) Appl. No.: 16/500,616

(22) PCT Filed: Apr. 10, 2018

(86) PCT No.: PCT/FI2018/050258
§ 371 (c)(1),
(2) Date: Oct. 3, 2019

(87) PCT Pub. No.: WO2018/189420
PCT Pub. Date: Oct. 18, 2018

(65) Prior Publication Data
US 2020/0029864 A1    Jan. 30, 2020

(30) Foreign Application Priority Data
Apr. 10, 2017 (FI) .................................... 20175334

(51) Int. Cl.
*A61B 5/00* (2006.01)
*A61B 5/11* (2006.01)
*G09B 19/00* (2006.01)

(52) U.S. Cl.
CPC .......... *A61B 5/1128* (2013.01); *A61B 5/0022* (2013.01); *A61B 5/0077* (2013.01); *G09B 19/003* (2013.01)

(58) Field of Classification Search
CPC ... A61B 5/1128; A61B 5/0022; A61B 5/0077; G09B 19/003
USPC ......................................................... 434/255
See application file for complete search history.

(56) References Cited

U.S. PATENT DOCUMENTS

| | | | |
|---|---|---|---|
| 5,760,389 A | 6/1998 | Biasi | |
| 5,888,179 A | 3/1999 | Singhal | |
| 5,897,457 A | 4/1999 | Mackovjak | |
| 8,363,927 B2 * | 1/2013 | Rutschnnann | A61B 5/0064 382/100 |
| 9,526,443 B1 | 12/2016 | Berme et al. | |
| 2006/0239538 A1 | 10/2006 | Sato et al. | |
| 2010/0037273 A1 | 2/2010 | Dressel et al. | |
| 2013/0028599 A1 | 1/2013 | Sone et al. | |
| 2014/0327610 A1 | 11/2014 | Athavale et al. | |
| 2016/0058649 A1 | 3/2016 | Fu et al. | |
| 2016/0098934 A1 | 4/2016 | Tinjust | |

FOREIGN PATENT DOCUMENTS

WO    0127563 A1    4/2001

* cited by examiner

*Primary Examiner* — Robert P Bullington
(74) *Attorney, Agent, or Firm* — Tarolli, Sundheim, Covell, & Tummino LLP (57) ABSTRACT

The invention relates to an optical measurement system (10) and measurement method for coaching an individual. The optical measurement system comprises a cloud database (8), a wireless communication device (7) and a vertical self-supporting equipment box (2) comprising a data processing device (20) comprising a computer program configured to measure ground contact and/or reaction time and position of a body part (1a) of a person (1) within a predetermined reaction area (6).

15 Claims, 5 Drawing Sheets

APPARATUS, METHOD AND SOFTWARE APPLICATION FOR PHYSICAL COACHING

RELATED APPLICATIONS

The present invention is a U.S. National Stage under 35 USC 371 patent application, claiming priority to Serial No. PCT/FI2018/050258, filed on 10 Apr. 2018; which claims priority of FI 20175334, filed on 10 Apr. 2017, the entirety of both of which are incorporated herein by reference.

TECHNICAL FIELD

The invention relates to an optoelectronic apparatus for measuring a ground contact and reaction time of a foot within a predetermined measurement region. The apparatus is adapted to perform tests needed for determining a fitness of an individual. The invention relates also to a computer program product implementing the method steps utilized during a measurement situation.

BACKGROUND

In the sports field evaluating a degree of preparation of athletics is one of the most widely used tests. First an athletic undergoes physical training period and after the training period measuring the contact and flight times during jumps or running steps can be made. A height of a jump or reaction time of the athlete can be calculated from the measurement data of the test situation.

This information may be utilized to evaluate for example the average developed energy and other biomechanical parameters.

The above-mentioned jump test may be accomplished by utilizing a measurement system including a computer provided with a chronometer program and a special jump mat. The size of the jump mat may have a size for example of 1 m×1 m. The jump mat may comprise several capacitive sensors spaced from one another by some centimetres. The person accomplishing the test must therefore perform the jumps on the jump mat. The person may make vertical jumps, drop jumps and repetitive jumps. When a person jumps on the jump mat both in the exertion phase and in the landing phase, the capacitive sensors of the jump mat generates an electronic signal that is transferred to the computer to be utilized in a performance analysis. From the measurement results may be calculated for example a height of a jump, reaction time or contact times between repetitive jumps.

An optical measurement system that may be utilized in evaluating a degree of preparation of a person is depicted in U.S. Pat. No. 5,760,389. The measurement system discloses two measurement bars. The dimensions of the measurement bars are 1000×25×25 mm. The measurement bars are arranged in parallel and face each other on a flat and smooth measurement surface. The measurement bars define a measurement area. The two measurement bars are spaced from one another by approximately no more than 3 meters. The measurement bars have an electrical connection. A connecting branches off from said electrical connection to a chronometer utilized in the measurement system.

The measurement bars differ from each other. One measurement bar discloses several optical transmitters and the other measurement bar discloses optical receivers. The functioning of the depicted measurement system requires that said measurement bars must be erected such a way that each one of the optical receivers of the receiver measurement bar can receive transmission only from one optical transmitter of the opposite located transmitter measurement bar. Therefore the measurement system of U.S. Pat. No. 5,760,389 must be erected on a flat smooth surface. If the utilized surface in a measurement place is not a flat and smooth then the measurement system does not function properly.

SUMMARY

The object of the present invention is to provide a measurement system, an apparatus and computer program by which measurements needed to evaluate a degree of preparation of a person can be made on any surface.

The objects of the invention are attained with an optical measurement system where boundaries of a measurement reaction area or reaction lines are projected by a projector utilizing visible light on a surface. A second optical transmitter scans the reaction area advantageously by infrared light. A camera unit receives pictures from body parts located inside the boundaries of the reaction area or crossing the reaction lines. A computer unit of the measurement system calculates from the camera pictures a place of the body part and a direction and movement speed of the body part. From these calculation results a contact time and reaction time of the person to be tested can be evaluated. From these measurement results can be analysed several physical performance characteristics of the tested person.

An aspect of the invention is an optical measurement system for coaching an individual, the optical measurement system comprising a cloud database, a wireless communication device and a vertical self-supporting equipment box comprising a data processing device configured to measure ground contact and/or reaction time and position of a body part of a person within a predetermined reaction area, wherein that self-supporting equipment box comprises     at least two direction signal lights on the vertical self-supporting equipment box;

a pattern projector on a vertical side of the vertical self-supporting equipment box configured to draw boundary lines of a reaction area or reaction lines by utilizing a predetermined visible light band     a monochromatic light source on the same vertical side of the self-supporting equipment box configured to illuminate the whole reaction area or reaction lines with a wave length that is outside the predetermined visible light band of the pattern projector     a camera on the same vertical side of the self-supporting equipment box configured to function as a picture data detector for the reaction area at least at the wave length of the monochromatic light source, and     a data processing device comprising         a processor         a memory including a computer program code         the memory and the computer program code configured to, with the processor, cause the data processing device at least to             determine a time and a place of a body part of the person in the reaction area by utilizing picture data of the camera             determine from consecutive body part determinations movement data of the body part, and             determine a ground contact and/or reaction time by utilizing the determined movement data.

Another aspect of the invention is a vertical self-supporting equipment box configured to be utilized in measuring ground contact and/or reaction time of a person on a reaction area, wherein the self-supporting equipment box comprises at least two direction signal lights on the vertical self-supporting equipment box a visible light pattern projector on a vertical side of the vertical self-supporting equipment box configured to define boundary lines of the reaction area or reaction lines with a predetermined visible light band a monochromatic light source on the same side of the vertical self-supporting equipment box for illuminating the whole reaction area or reaction lines with a wave length that is outside the predetermined visible light band of the pattern projector a camera on the same side of the vertical self-supporting equipment box configured to function as a picture data detector for the reaction area at least at the wave length of the monochromatic light source, and a data processing device configured to determine a ground contact and/or reaction time of the person by utilizing picture data of the camera.

A third aspect of the invention is a method for measuring ground contact and/or reaction time of a person on a reaction area, wherein the method comprises following steps:

turning on a visible light pattern projector, a monochromatic light source and a camera the visible light pattern projector on a vertical side of the vertical self-supporting equipment box drawing boundary lines of the reaction area or reaction lines with a predetermined visible light band the monochromatic light source on the same side of the vertical self-supporting equipment box illuminating the whole reaction area or reaction lines with a wave length that is outside the predetermined visible light band of the pattern projector a camera on the same side of the vertical self-supporting equipment box functioning as a picture data detector for the reaction area at least at the wave length of the monochromatic light source determining a time and a place of a body part of the person on the reaction area by utilizing picture data of the camera determining from consecutive body part determinations movement data of the body part determining a ground contact and/or reaction time of the person by utilizing the determined movement data, and saving the contact and reaction time measurement results to a memory of a data processing device and stopping the measurement session.

A fourth aspect of the invention is a computer program product comprising computer program code means adapted to perform the following program code steps when said program is executed on a processor of a data processing device, wherein the computer program comprises code means for turning on a visible light pattern projector, a monochromatic light source and a camera code means for drawing (boundary lines of the reaction area or reaction lines with a predetermined visible light band by controlling a visible light pattern projector code means for illuminating the whole reaction area or reaction lines with one wave length by controlling a monochromatic light source code means for a camera functioning as a picture data detector for the reaction area or reaction lines at least at the wave length of the monochromatic light source code means for determining a time and a place of a body part of the person on the reaction area by utilizing picture data of the camera code means for determining from consecutive body part determinations movement data of the body part code means for determining a ground contact and/or reaction time of the person by utilizing the determined movement data, and code means for saving the contact and reaction time measurement results to a memory of a data processing device and stopping the measurement session.

An advantage of the invention is that the measurement of contact and reaction times of a person to be tested can be made on any surface.

Another advantage of the invention is that the measurement system is lightweight and movable.

A further advantage of the invention is that the measurement system is easy to use.

Further scope of applicability of the present invention will become apparent from the detailed description given hereafter. However, it should be understood that the detailed description and specific examples, while indicating advantageous embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and accompanying drawings which are given by way of illustration only, and thus are not limitative of the present invention and wherein

FIG. 4 shows as an exemplary a flow chart the main operational steps of a reaction time measurement according to the invention; and.

DETAILED DESCRIPTION OF THE DRAWINGS

In the following description, considered embodiments are merely exemplary, and one skilled in the art may find other ways to implement the invention. Although the specification may refer to "an", "one; or "some" embodiment(s) in several locations, this does not necessarily mean that each such reference is made to the same embodiment(s), or that the feature only applies to a single embodiment or all embodiments. Single feature of different embodiments may also be combined to provide other embodiments.

Figure 1A:
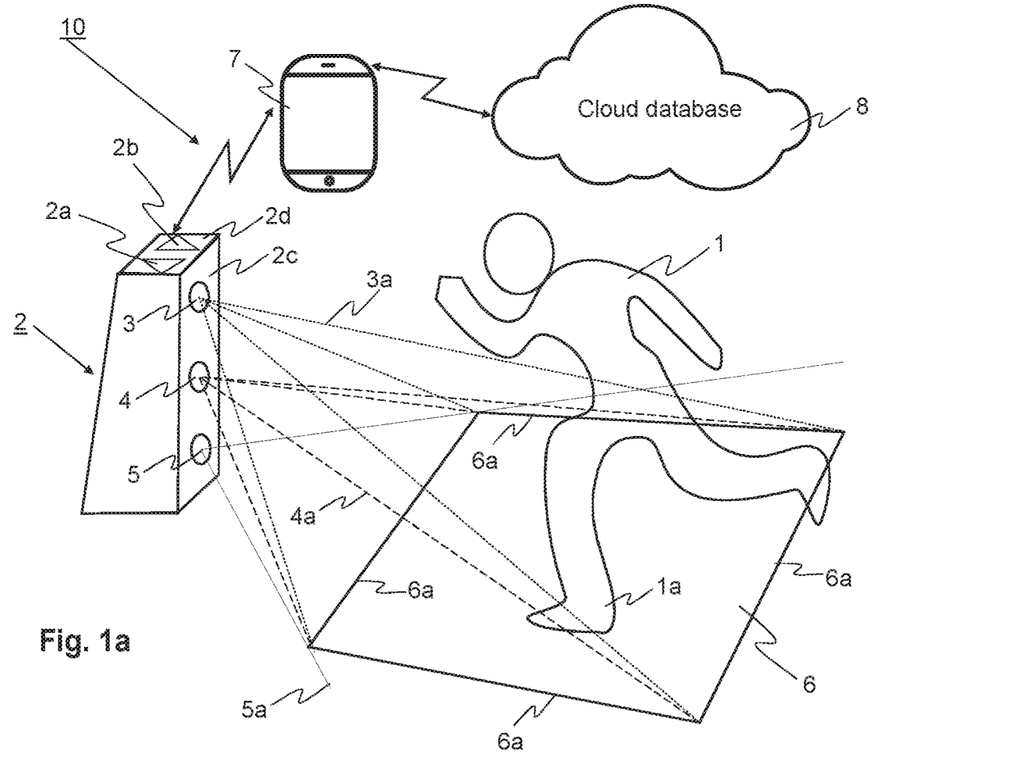
FIG. 1a shows schematically the optical performance measurement arrangement according to a first embodiment of the invention.

FIG. 1a depicts an optical measurement system 10 according to the invention that may be utilized for coaching an individual, for example an athletic.

The depicted optical measurement system 10 may be utilized also in other tests for example in following coaching cases: testing physiological recovery of a person, different kind of jump tests, elasticity test, explosive strength test, reaction time test, T-test, ground contact time, stride angle, speed and explosive strength, quickness and agility, step length, unbalance index and body composition.

The optical measurement system 10 for coaching advantageously comprises a self-supporting equipment box 2 comprising three optical measurement devices 3, 4 and 5, a wireless communication device 7 and a cloud database 8 for storing measurement results. Advantageously the self-supporting equipment box has a greater vertical direction than a horizontal direction and therefore in the following description the self-supporting equipment box may be also called a vertical self-supporting equipment box.

The wireless communication device 7 may be a mobile phone such as a prior art GSM, GPRS or UMTS terminal device, a tablet, a laptop computer or a personal digital assistant for example. The wireless communication device 7 may be utilized to control measurement sessions of the optical measurement system 10. It advantageously also functions as a communication repeater that transmits measurement results from a data processing device 20 (FIGS. 2 and 3) of the vertical self-supporting equipment box 2 to the cloud database 8.

The exemplary vertical self-supporting equipment box 2 in FIG. 1a advantageously comprises four walls or sides and at least one of them is essentially a plane-like vertical side 2c. On the vertical side 2c are advantageously installed three optical measurement devices that are needed in the measurements: a reaction area pattern projector 4 that draws boundary lines 6a of the reaction area 6, a camera 3 and a monochromatic light source 5.

Figure 2:
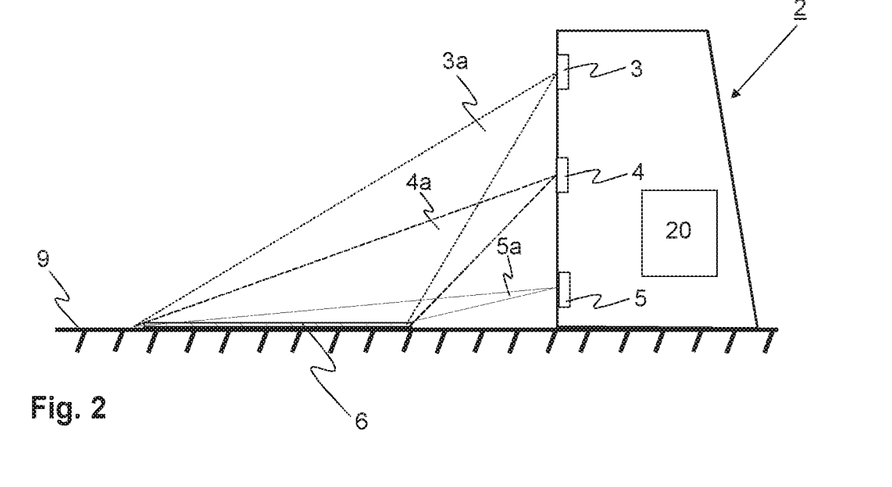
FIG. 2 shows schematically an installation of an equipment box on the ground belonging to the optical measurement arrangement according to the invention.

The pattern projector 4 according to the invention draws boundary lines 6a of a reaction area 6 on the ground surface 9 (FIG. 2). The pattern projector 4 may also draw text or logo of the apparatus on the reaction area 6. The pattern projector 4 utilizes a predetermined band of visible light 4a. In FIG. 1a it can be seen that a person 1 is running or jumping on the reaction area 6 whose boundary lines 6a are visible to the person 1.

The utilized predetermined band 4a of light is visible to humans on any surface. Therefore the ground surface 9 may be an even floor or uneven sport field, for example a football arena. A technical effect of the present invention is that the surface 9, on which the reaction area 6 may be imaged, need not to be even or horizontal.

The reaction area 6 is illuminated also from a monochromatic light source 5 that may be a laser for example. The monochromatic light source 5 is advantageously on the same vertical side of the vertical self-supporting equipment box 2 as the pattern projector 4. The monochromatic light source 5 illuminates at least the whole reaction area 6 with a wave length 5a that advantageously is outside the predetermined band of visible light 4a that the pattern projector 4 utilizes.

Movements of a foot 1a of the person 1 are advantageously detected by the camera 3. The camera 3 is located advantageously on the same vertical side of the self-supporting equipment box 2 as the pattern projector 4 and monochromatic light source 5. Camera 3 may be located either above, below or beside the pattern projector 4. However the camera 3 is above a plane that monochromatic light source 5 illuminates above the ground 9.

The camera 3 can advantageously take pictures at least a wave length 3a that is equal as the wave length 5a that the monochromatic light source 5 transmits. In that advantageous embodiment the camera 3 is an infrared light camera.

However the invention is not limited to utilize an infrared light camera. Also a camera functioning on visible light band may be utilized.

The operating rate of the camera 3 is high enough to detect a contact time of the foot 1a of the person 1 on a surface of the reaction area 6. The operating rate of the camera may advantageously be only some p seconds. The ground contact time calculation begins when the foot 1a comes from above and touches the ground 9. The camera 3 detects this event when the foot 1a intersects the illuminated plane that the monochromatic light source 5 has imaged above the reaction area 6. The ending time of the ground contact time the camera 3 detects when the foot 1a rises from the ground surface above the illuminated plane that the monochromatic light source 5 has imaged above the reaction area 6.

The vertical self-supporting equipment box 2 comprises also at least two signal lights 2a and 2b. In the example of FIG. 1a the signal lights are installed on an upper horizontal side 2d of the vertical self-supporting equipment box 2. The signal light 2a may generate a light signal to left as seen from the position of the person 1. Correspondingly the signal light 2b may generate a light signal to right as seen from the position of the person 1. In the example of FIG. 1a the person 1 gets a movement direction command by one or the other signal light.

It is obvious to a person skilled in the art that there may be several signal lights than two and that the signal lights may locate also on the same vertical side where the camera 3 is (i.e. on front wall) or also on the left and right side walls.

Some examples of the test known in the art that may be accomplished by the optical measurement system 10 depicted in FIG. 1a are shortly depicted next.

When the person 1 is making a jump test then in that case the ground contact time calculation begins when the foot 1a rises from the ground surface of the reaction area 6. The ending time of the ground contact time measurement the camera 3 detects when the foot 1a comes from above and touches the ground 9. The camera 3 detects these two measurement events when the foot 1a intersects the illuminated plane that the monochromatic light source 5 has imaged above the reaction area 6.

In static jump test (SJ) the person 1 performs the test from semi-squat position at 90° knee angle and hands on the hips and trunk as vertical as possible. The person jumps up as explosively as possible holding hands on the hips and extending the hips and knees. The person should land with the balls of the feet keeping the knees straight at the point of landing. By this test can be evaluated speed and explosive strength.

A static jump test may be made also with extra weights that the person 1 carries.

In a starting position of a counter movement jump test (CMJ) the person 1 stands straight with hands on the hips. The person squads rapidly down to a knee angle of 90°. Then the person jumps explosively as possible and maintains the hands on the hips. During ascending phase the person should keep the upper body as erect as possible. The person should land on the reaction area with the balls of the feet keeping the knees straight.

In drop jump test (DJ) the person 1 jumps from stairs or a podium several times from different heights. During the jumps the person keeps the hands on the hips. The person should land on the reaction area with straight knees on the balls of the feet. Then the person should squat down immediately and jump up as explosively as possible. Landing should be done in the same manner as in the static jump test or counter movement jump test.

Elasticity of the person 1 can be calculated from measurement results of the counter movement jump test and the static jump test.

In a reactivity (stiffness) test the person 1 performs several explosive jump tests. The person keeps knees as straight as possible and lands on the reaction area with the balls of the feet with stiff ankles. The person should use a forceful upward motion of the arms during the jump. The idea of the test is to keep the ground contact time as short as possible while maximizing the flight time.

In a take-off reaction test the person 1 stands on the reaction area knees slightly bent, hands resting on the hips and head up facing the vertical self-supporting measurement box 2. The person reacts to a signal of signal light 2a or 2b of the vertical self-supporting measurement box 2 by taking a direction step with the leg in the direction of the signal light 2a or 2b. The person steps outside the reaction area while simultaneously pivoting and pushing of with the opposite leg. After that the person accelerates as hard as possible and crosses a reaction or timing line drawn by the pattern projector 4. The test is repeated several times in both directions.

By the optical measurement system 10 depicted in FIG. 1a can be measured at least a response time and response force of the person 1 that has got the movement command. From the measurement data may be analysed for example a physiological recovery state of a person, ground contact time, reaction time, stride angle, speed and explosive strength, acceleration and speed, quickness and agility, step length, unbalance index and body composition.

Figure 1B:
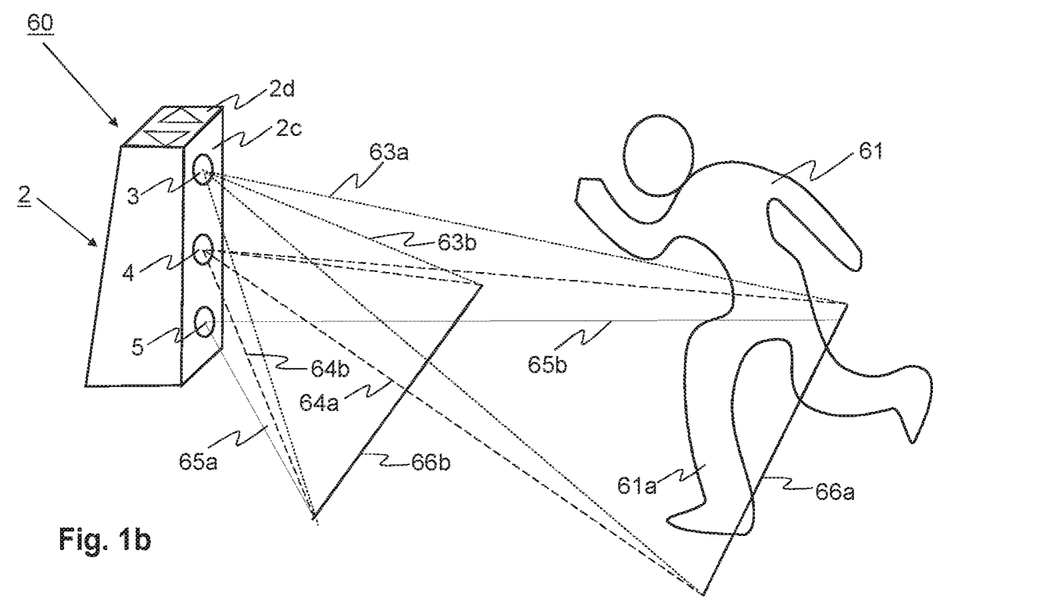
FIG. 1b shows schematically the optical performance measurement arrangement according to a second embodiment of the invention.

FIG. 1b depicts an optical measurement system 60 according to the invention that may be utilized for acceleration and speed tests.

In the embodiment depicted in FIG. 1b the pattern projector 4 according to the invention draws boundary at least two reaction lines 66a and 66b on the ground surface 9 (FIG. 2). The reaction lines 66a and 66b are advantageously drawn so wide that it is easy to hit the foot 61a on the drawn reaction line 66a and 66b. The pattern projector 4 utilizes a predetermined band of visible light 64a and 64b when drawing the reaction lines 66a and 66b. In FIG. 1b it can be seen that a person 61 is running and crossing at least two reaction lines 66a and 66b that are visible to the person 61.

The reaction lines 66a and 66b are illuminated also from a monochromatic light source 5. The monochromatic light source 5 illuminates (references 65a and 65b) at least same areas of the two reaction lines 66a and 66b that the pattern projector 4 has drawn. The utilized wave length of the monochromatic light source 5 is advantageously outside the predetermined band of visible light 64a and 64b that the pattern projector 4 utilizes. The invention is not limited only to two reaction lines.

Movements of a foot 61a of the person 61 are advantageously detected by the camera 3. In the advantageous embodiment of FIG. 1b the self-supporting equipment box 2 may comprise two cameras side by side. By two cameras it is possible to define a distance to the person 61 during a test situation.

The camera 3 or cameras can take pictures at least a wave length 63a that is advantageously equal to the wave length 65a and 65b that the monochromatic light source 5 transmits. In that advantageous embodiment the camera 3 is an infrared light camera. However the invention is not limited to utilize an infrared light camera. Also a camera functioning on visible light band may be utilized.

The operating rate of the camera 3 is high enough to detect a contact time of the foot 1a of the person 61 on the reaction lines 66a and 66b. The operating rate of the camera may advantageously be only some μ seconds. The ground contact time calculation begins when the foot 1a comes from above and touches the ground 9 on the reaction lines 66a and 66b. The camera 3 detects this event when the foot 61a intersects the drawn reaction lines 66a and 66b that also the monochromatic light illuminated source 5 has illuminated. The ending time of the ground contact time the camera 3 detects when the foot 61a rises from the ground surface 9 above the illuminated plane that the monochromatic light source 5 has imaged above the reaction lines 66a and 66b.

An acceleration and speed test depicts an ability of the person 61 to take-off, to accelerate and to sprint. The acceleration test may vary from 5 to 10 meters. A test to measure transition to speed phase may be between 10 to 30 metres and maximum speed test are usually up to 60 meters.

In the above mentioned take-off, to accelerate and to sprint tests the optical systems of the vertical self-supporting equipment box 2 advantageously draws several parallel reaction lines on the ground. When the person 61 starts the test he or she crosses the first reaction line 66a by the foot 61a. This starts the clock belonging to the vertical self-supporting equipment box 2. During acceleration phase and sprint phase the person 61a may cross several reaction lines (not shown in FIG. 1b). Each crossing time the clock saves a time mark. Finally the person 61 crosses the last reaction line 66b and the clock stops and the starting time, all crossing times and the stopping time are utilized in the acceleration and speed calculations.

Figure 1C:
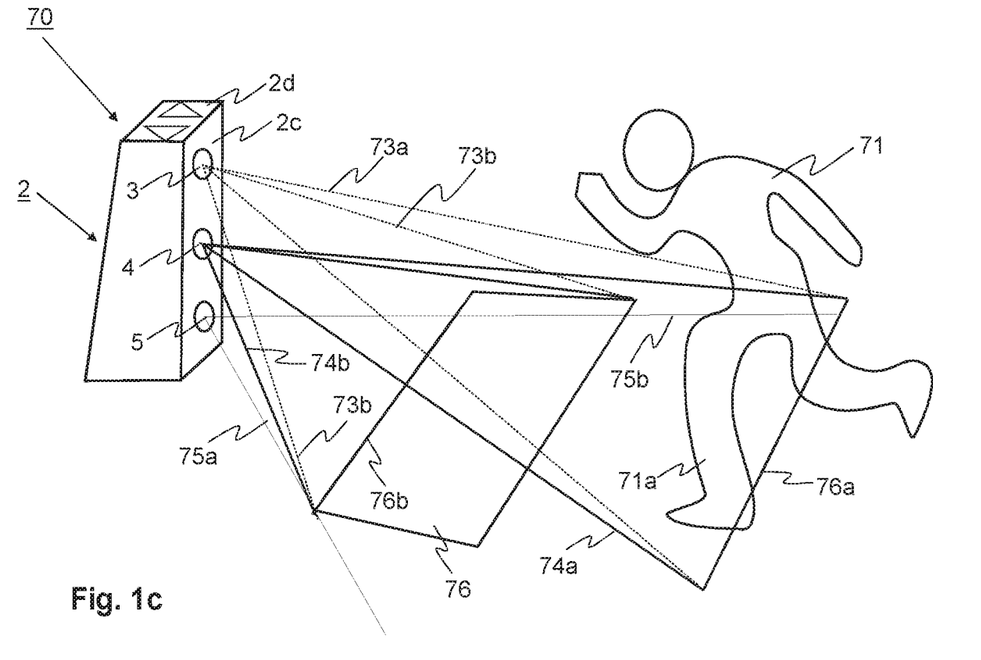
FIG. 1c shows schematically the optical performance measurement arrangement according to a third embodiment of the invention.

FIG. 1c depicts a third advantageous optical measurement system 70 according to the invention that may be utilized for acceleration and speed tests.

In the embodiment depicted in FIG. 1c the pattern projector 4 according to the invention draws boundary a reaction lines 76a and a reaction area 76 on the ground surface 9 (FIG. 2). The reaction area 76 in the running direction is advantageously wider than the step length of the person 71 under test. The width of the reaction area 76 can advantageously be adapted to a known step length of the person 71. By that it is secured that at least one step of the person 71 is detected on the reaction area 76.

The pattern projector 4 utilizes a predetermined band of visible light 74a and 74b when drawing the reaction line 76a and the borderlines of the reaction area 76. In FIG. 1c it can be seen that a person 71 is starting his or hers run. In the starting moment his or hers foot 71a crosses the reaction line 76a that is visible to the person 71.

The reaction line 76a and the reaction area 76 are illuminated also from a monochromatic light source 5. The monochromatic light source 5 illuminates (references 75a and 75b) at least the reaction line 76a and the reaction area 76 that the pattern projector 4 has drawn wholly. The utilized wave length of the monochromatic light source 5 is advantageously outside the predetermined band of visible light 74a and 74b that the pattern projector 4 utilizes.

Movements of a foot 71a of the person 71 are advantageously detected by the camera 3. In the advantageous embodiment of FIG. 1c the self-supporting equipment box 2 may comprise two cameras side by side. By two cameras it is possible to define a distance to the person 71 during a test situation.

The camera 3 or cameras can take pictures at least a wave length 73a that is advantageously equal to the wave length 75a and 75b that the monochromatic light source 5 transmits. In that advantageous embodiment the camera 3 is an infrared light camera. However the invention is not limited to utilize an infrared light camera. Also a camera functioning on visible light band may be utilized.

The operating rate of the camera 3 is high enough to detect a contact time of the foot 71a of the person 1 on the reaction line 76a and on the reaction area 76. The ground contact time calculation begins when the foot 71a comes from above and touches the ground 9 either on the reaction line 76a or reaction area 76. The camera 3 detects this event when the foot 71a intersects the illuminated plane that the monochromatic light source 5 has imaged above the reaction line 76a and the reaction area 76. The ending time of the ground contact time the camera 3 detects when the foot 71a rises from the ground surface above the illuminated plane that the monochromatic light source 5 has imaged above the reaction line 76a and the reaction area 76.

FIG. 2 shows the exemplary vertical self-supporting equipment box 2 as seen from side. It stays on the ground 9. Inside vertical self-supporting equipment box 2 is depicted a data processing device 20. The data processing device 20 controls the functioning of the camera 3, the reaction pattern projector 4 and the monochromatic light source 5. The data processing device 20 may advantageously define a utilized size of the created reaction pattern area 6 by giving control commands to the camera 3, reaction pattern projector 4 and monochromatic lights source 5. The data processing device 20 advantageously direct the monochromatic light source 5 that the illuminated plane intersects the ground plane 9 beyond the border lines 6a of the reaction area 6.

Figure 3:
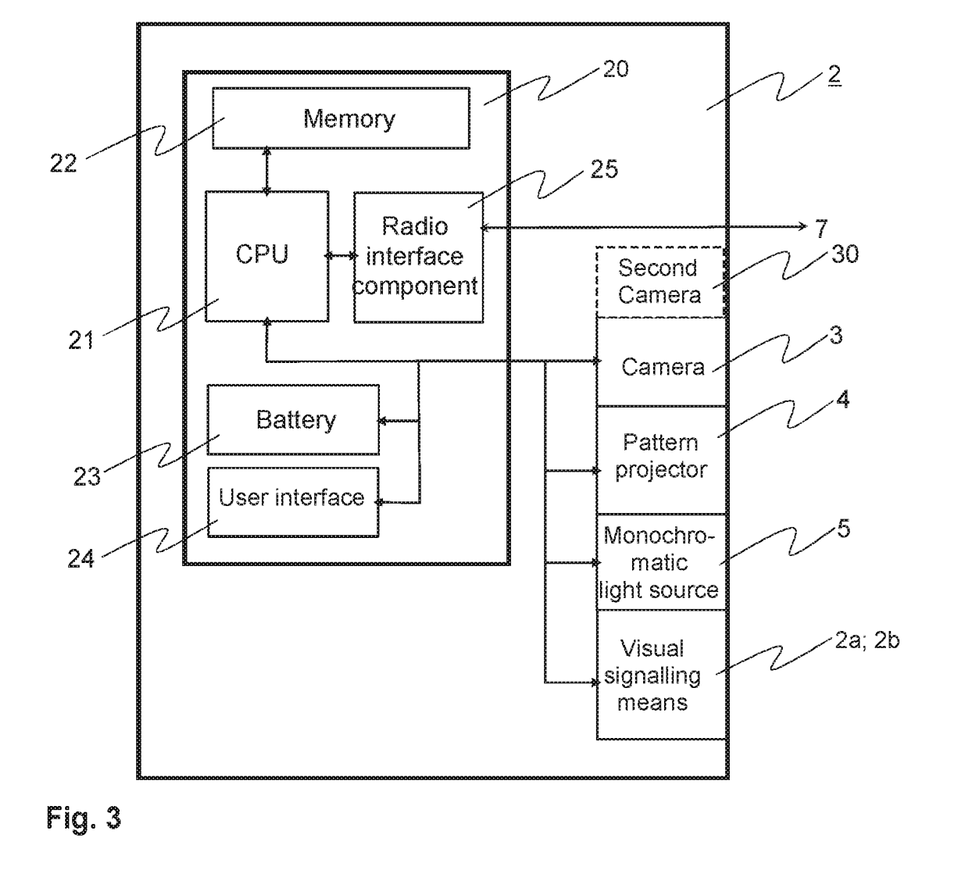
FIG. 3 shows the main electronic elements installed in the equipment box by way of example.

FIG. 3 shows, by way of example, the functional main parts of a data processing device 20 that controls functioning of the vertical self-supporting equipment box 2.

The data processing device 20 uses an antenna (not shown in FIG. 3) in the transmission and reception of signals with the wireless communication device 7. The radio interface components 25 advantageously comprises communication means needed in Bluetooth®, ZigBee® or WLAN connections with the wireless communication device 7.

In the data processing device 20 is a central processing unit 21 that controls operations of the camera 3, pattern projector 4 and monochromatic light source 5. It controls also functioning of the memory 22, in which the software application required in the implementation of the measurement method according to the invention can advantageously be stored. Also the measurement results may be stored at least temporally in the memory 22.

In FIG. 3 is shown also an optional second camera 30 that may be utilized in tests.

The data processing device 20 may also comprise a user interface 24. It comprises at least a display and some functional buttons.

The data processing device 20 comprises also a battery 23. The processor 21, camera 3, pattern projector 4 and monochromatic light source 5 get electrical energy needed in function from the battery 23.

Figure 4:
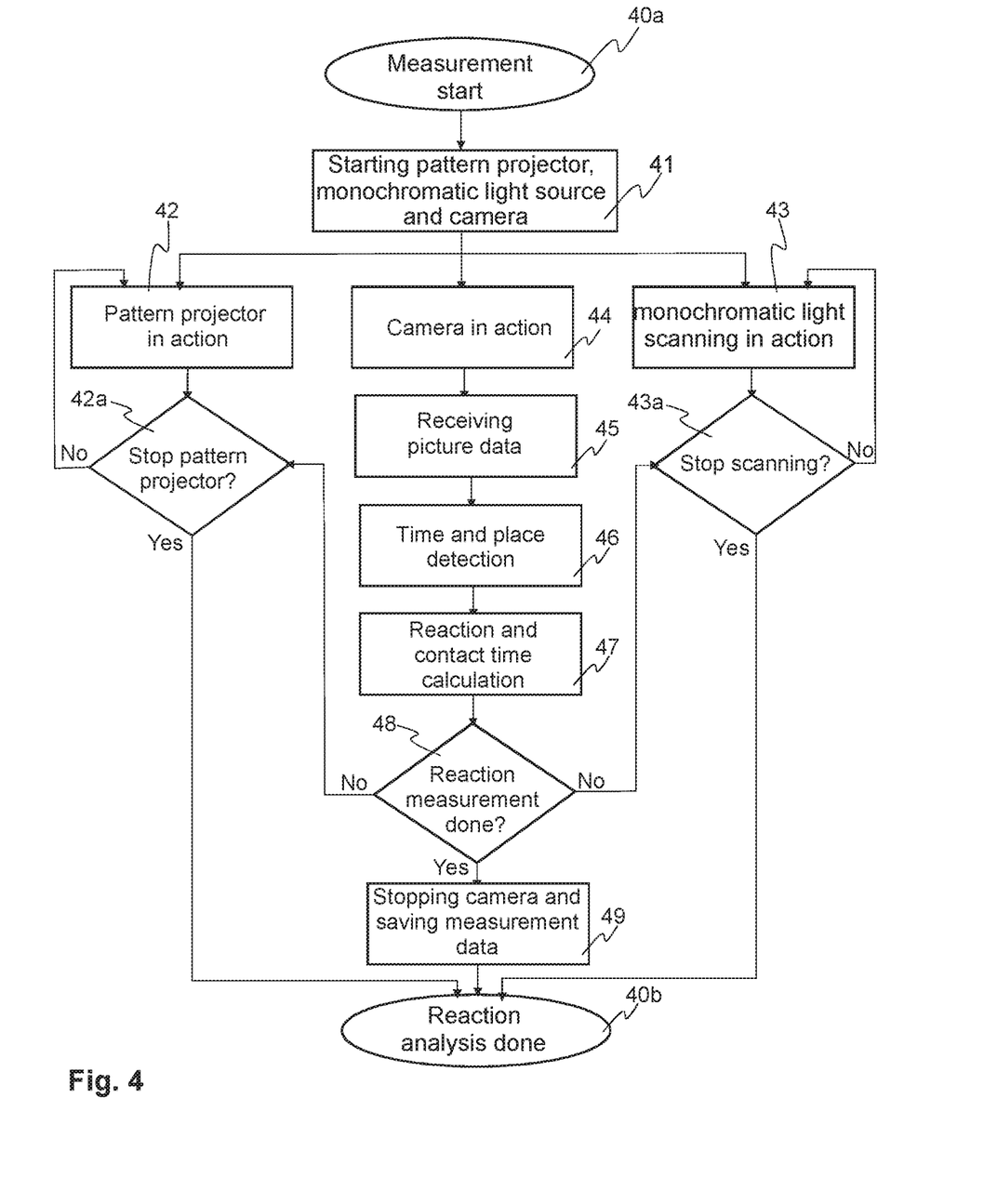

In FIG. 4 the main steps of the method according to the invention when making different kind of jump test are shown as an exemplary flow chart.

The measurement process starts in step 40a where a user of the physical coaching arrangement according to the invention activates the measurement system 10 advantageously by giving a starting command by a wireless communication device 7. In one advantageous embodiment the user of the wireless communication device 7 may advantageously define also a size of the reaction area 6. In another advantageous embodiment the wireless communication device retrieves size information that is needed for defining the size of the reaction area 6 from the cloud database 8. In the same context the wireless communication device 7 may advantageously also retrieve earlier measurement results of the person 1 to be tested.

Advantageously in step 40a it is also selected a test method for the test session. Some alternatives of possible physical tests are a static jump test, counter movement jump test, drop jump test, elasticity reactivity (stiffness) test, take-off reaction test and T-test.

In step 41 the central processing unit 21 of the data processing device 20 in the vertical self-supporting equipment box 2 starts the pattern projector 4, monochromatic light source 5 and camera 3. In this step the central processing unit 21 advantageously aligns angle of views of the pattern projector 4, monochromatic light source 5 and camera 3 so that they are compatible in the test session to be started. After that the test process moves to concurrent steps 42, 43 and 44 where the pattern projector 4, monochromatic light source 5 and camera 3 are in active state.

In step 42 the pattern projector 4 draws boundary lines 6a of the defined reaction area 6. Time to time it is checked if the measurement session is in active state in step 42a. If the checking result is that the pattern projector 4 should not be stopped, the process returns back to step 42.

In step 43 the monochromatic light source 5 illuminates defined reaction area 6. Time to time it is checked if the measurement session is in active state in step 43a.

If the checking result is that illumination of the reaction area 6 should not be stopped, the process returns back to step 43.

In step 44 the camera 3 is taking pictures that include the whole area of the reaction area 6. Advantageously the camera 3 is sensitive to at least the wavelength of the monochromatic light source 5.

The following steps depict a situation where the person is accomplishing a T-test that measures the person's ability to react to a given stimulus. In other alternative tests the measurement process may in some details vary from the method steps of the T-test depicted in the description below.

In the exemplary T-test situation in FIG. 1b in step 45 the person 1 under test steps on the reaction area 6 and after that by one of the signalling lights 2a or 2b a movement direction command is given to the person 1. The starting of the signalling light 2a or 2b starts a chronometer that records a starting time of the measurement session. The starting time mark is advantageously saved in the memory 22 of the data processing device 20.

The camera 3 advantageously receives picture data from which the foot 1a of the person may be detected at least at the moment when the foot intersects the illumination plane that the monochromatic light source 5 has been created above the reaction area 6.

Step 46 discloses at least two sub-steps. In a first sub-step a place of the foot 1a on the reaction area 6 is defined from picture data of camera 3. Also a first time mark defining a ground contact of the foot 1a is defined when the foot 1a intersect the illumination plane that the monochromatic light source 5 has created. The first time mark is then stored in the memory 22 of the data processing device 20.

In a second sub-step of step 46 a second time mark is defined when the foot 1a rises from the ground so high that the foot 1a does not anymore intersect the illumination plane that the monochromatic light source 5 has created. Also the second time mark is stored in the memory 22 of the data processing device 20.

In step 47 the data processing device 20 calculates from the starting time mark, the first time mark and second time mark at least a ground contact time and/or reaction time of the person under test. The data processing device 20 stores the at least temporary calculated ground contact and reaction times to the memory 22.

In one advantageous embodiment the data processing device 20 sends at least the calculated ground contact and reaction times via the radio interface component 25 to the wireless communication device 7.

After data transmission to the wireless communication device 7 it is checked if all needed measurements are made in step 48. If the answer in step 48 is "NO" then a command to the pattern projector 4 and monochromatic light source 5 is sent not to stop functioning message (steps 42a and 43a).

If the answer in step 48 is "YES" then the pattern projector 4 and monochromatic light source 5 will not receive commands not to stop functioning message (steps 42a and 43a). In the next checking moment in steps 42a and 43a the pattern projector 4 and monochromatic light source 5 will be shut down for saving energy of the battery 23 of the vertical self-supporting equipment box 2.

In step 49 it is first checked that measurement results are transferred from memory 22 of the data processing device 20 to the wireless communication device 7. If the transfer has been made, then also the camera 3 is shut down and measurement session ends in step 40b.

In other jump tests the method steps comprises at least one method step to define foots rising from the ground and another method step to define foots landing to the ground. Some tests may comprise several jumps one after the other. In those tests each rising time and landing time of the foot is detected and utilized in calculating for example ground contact and reaction times.

Figure 5:
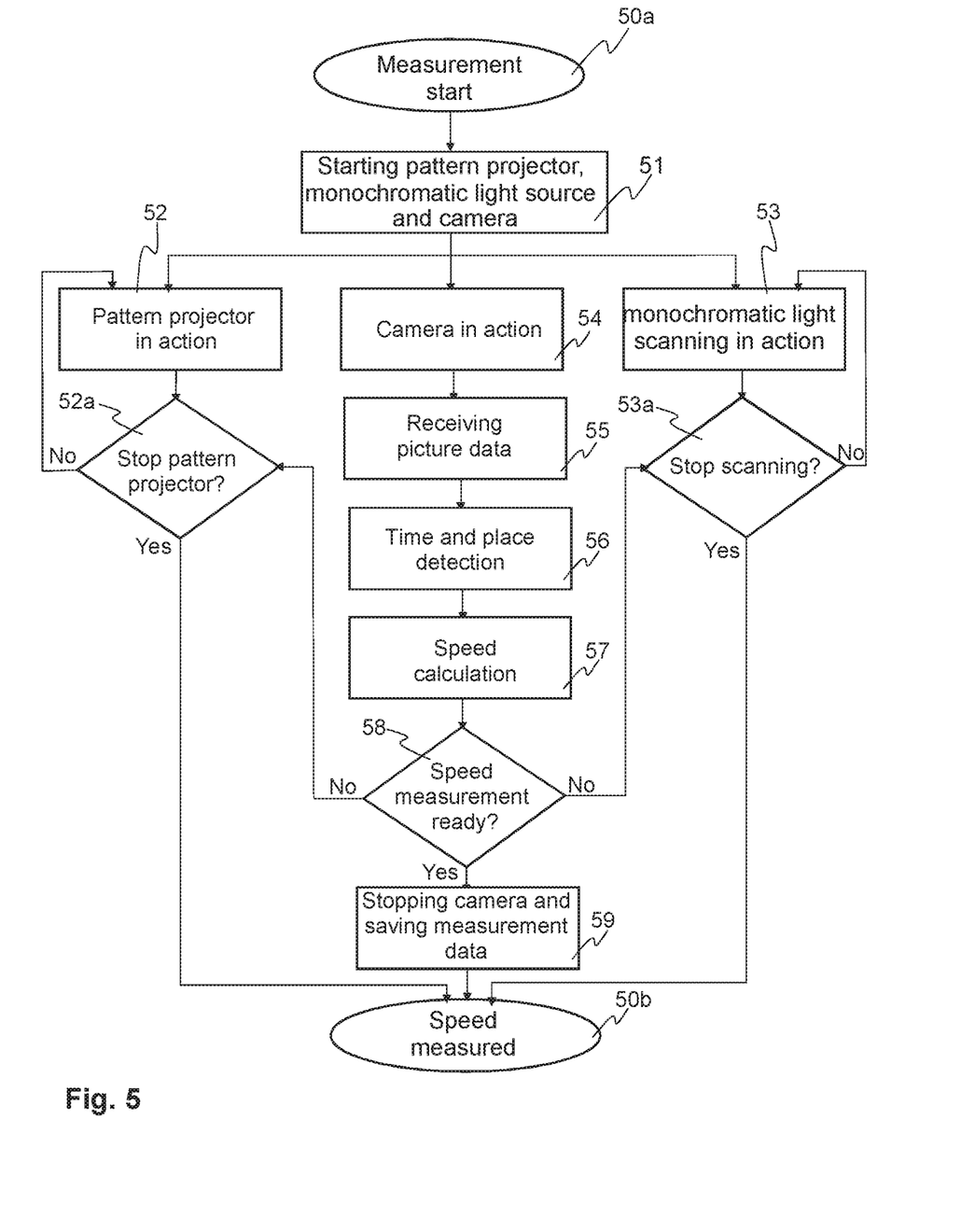
FIG. 5 shows as an exemplary a flow chart the main operational steps of a speed or acceleration measurement according to the invention.

In an exemplary flow chart of FIG. 5 the main steps of the method according to the invention are shown when making acceleration and speed tests by utilizing the measurement system of FIG. 1b or 1c.

The measurement process starts in step 50a where a user of the physical coaching arrangement according to the invention activates the measurement system 60 advantageously by giving a starting command by a wireless communication device 7. Advantageously in step 50a it is also selected a test method for the acceleration and speed session.

In step 51 the central processing unit 21 of the data processing device 20 in the vertical self-supporting equipment box 2 starts the pattern projector 4, monochromatic light source 5 and camera 3. In this step the central processing unit 21 advantageously aligns angle of views of the pattern projector 4, monochromatic light source 5 and camera 3 so that they are compatible in the test session to be started. After that the test process moves to concurrent steps 52, 53 and 54 where the pattern projector 4, monochromatic light source 5 and camera 3 are in active state.

In step 52 the pattern projector 4 draws reaction lines 66a and 66b or the reaction line 76a and the reaction area 76 on the ground. Time to time it is checked if the measurement session is in active state in step 52a. If the checking result is that the pattern projector 4 should not be stopped, the process return back to step 52.

In step 53 the monochromatic light source 5 illuminates the areas 66a and 66b or the reaction line 76a and the reaction area 76 that the pattern projector 4 has drawn.

Time to time it is checked if the measurement session is in active state in step 53a. If the checking result is that illumination of the reaction lines and reaction area should not be stopped, the process return back to step 53.

In step 54 the camera 3 is taking pictures that include at least the areas 66a and 66b or the reaction line 76a and the reaction area 76 drawn by the pattern projector 4. Advantageously the camera 3 is sensitive to at least the wavelength of the monochromatic light source 5.

In FIGS. 1b and 1c in step 55 the person 61 or 71 under test accelerates over a first reaction line 66a or 76a and after a command given by the signalling lights of the self-supporting equipment box 2. This starts a chronometer that records a starting time of the measurement session. The starting time mark is advantageously saved in the memory 22 of the data processing device 20.

The camera 3 advantageously receives picture data from which the foot 61a of the person 61 or the foot 71a of the person 71 may be detected at least at the moment when the foot intersects the illumination plane that the monochromatic light source 5 has been created above the first reaction line 66a or 76a.

Step 56 discloses at least two sub-steps. In a first sub-step a place of the foot 61a or 71a crossing the reaction line 66a or 76a is defined from picture data of camera 3. Also a first time mark defining is defined when the foot 61a or 71a intersect the illumination plane that the monochromatic light source 5 has created over the first reaction line 66a or 76a. The first time mark is then stored in the memory 22 of the data processing device 20.

In a second sub-step of step 56 a second time mark is defined when the foot 61a crosses either another reaction line, for example reaction line 66b in FIG. 1b or arrives to the reaction area 76 in FIG. 1c. Also the second time mark is stored in the memory 22 of the data processing device 20. Also other time marks can be defined and saved correspondingly.

In step 57 the data processing device 20 calculates from the starting time mark, and other time marks acceleration and speed of the person 61 under test. The data processing device 20 stores the at least temporary calculated acceleration and speed values to the memory 22.

In one advantageous embodiment the data processing device 20 sends at least the calculated ground acceleration and speed values via the radio interface component 25 to the wireless communication device 7.

After data transmission to the wireless communication device 7 it is checked if all needed acceleration and speed measurements are made in step 58. If the answer in step 48 is "NO", then a command to the pattern projector 4 and monochromatic light source 5 is sent not to stop functioning message (steps 52a and 53a).

If the answer in step 58 is "YES", then the pattern projector 4 and monochromatic light source 5 will not receive commands not to stop functioning message (steps 52a and 53a). In the next checking moment in steps 52a and 53a the pattern projector 4 and monochromatic light source 5 will be shut down for saving energy of the battery 23 of the vertical self-supporting equipment box 2.

In step 59 first it is checked that measurement results are transferred from memory 22 of the data processing device 20 to the wireless communication device 7. If the transfer has been made, then also the camera 3 is shut down and the acceleration and speed measurement session ends in step 40b.

Any of the steps described or illustrated in FIGS. 4 and 5 may be implemented using executable instructions in a general-purpose or special-purpose processor and stored on a computer-readable storage medium (e.g., disk, memory, or the like) to be executed by such a processor. References to 'computer-readable storage medium' and 'computer' should be understood to encompass specialized circuits such as field-programmable gate arrays, application-specific integrated circuits (ASICs), USB flash drives, signal processing devices, and other devices.

The cloud database 8 may be accomplished by one or more servers. Each server has one or more processors. The processor or processor means can comprise an arithmetic logic unit, a group of different registers and control circuits. A data storing arrangement, such as a memory unit or memory means, whereon computer-readable information or programs or user information can be stored, has been connected to the processor means. The memory means typically contain memory units, which allow both reading and writing functions (Random Access Memory, RAM), and memory units containing non-volatile memory, from which data can only be read (Read Only Memory, ROM). The measurement data and calculated reaction and ground contact times are advantageously stored in the memory.

Some advantageous embodiments according to the invention were described above. The invention is not limited to the embodiments described. The inventive idea can be applied in numerous ways within the scope defined by the claims attached hereto.

The invention claimed is:

1. An optical measurement system for coaching an individual, the optical measurement system comprising:
   a cloud database;
   a wireless communication device; and
   a vertical self-supporting equipment box comprising a data processing device configured to measure a ground contact and a reaction time and position of a body part of a person within a predetermined reaction area;
wherein the vertical self-supporting equipment box comprises:
   at least two direction showing signal lights on the vertical self-supporting equipment box;
   a pattern projector on a vertical side of the vertical self-supporting equipment box configured to draw boundary lines of an optically drawn, horizontal reaction area or reaction lines on a ground surface by utilizing a predetermined visible light band;
   a monochromatic light source on the vertical side of the vertical self-supporting equipment box configured to illuminate the optically drawn, horizontal reaction area as a whole or reaction lines on the ground surface with a wavelength that is outside the predetermined visible light band of the pattern projector;
   a camera on the vertical side of the vertical self-supporting equipment-box configured to function as a picture data detector for the optically drawn, horizontal reaction area on the ground surface at least at the wavelength of the monochromatic light source; and;
   a data processing device comprising:
   a processor;
   a memory including a computer program code configured to, with the processor, cause the data processing device at least to:
      determine a time and a place of the body part of the person in the optically drawn, horizontal reaction area by utilizing picture data of the camera;
      determine, from consecutive body part determinations, a movement data of the body part; and
      determine the ground contact and the reaction time by utilizing the determined movement data.

2. The optical measurement system according to claim 1, wherein the ground contact and the reaction time is measured in T-test, static jump test, counter movement jump test, drop test, elasticity test, stiffness test or take-off reaction test.

3. The optical measurement system according to claim 1, wherein the ground contact times are measured in an acceleration or a speed test.

4. The optical measurement system according to claim 1, wherein the wireless communication device is configured to:
   control a measurement session of the optical measurement system; and
   relay measurement results from the data processing device to the cloud database.

5. The optical measurement system according to claim 1, wherein the wireless communication device is a mobile phone, tablet, laptop computer or personal digital assistant.

6. A vertical self-supporting equipment box configured to be utilized in measuring a ground contact and a reaction time of a person on an optically drawn, horizontal reaction area;
   wherein the vertical self-supporting equipment box comprises:
      at least two direction showing signal lights on the vertical self-supporting equipment box;
      a visible light pattern projector on a vertical side of the vertical self-supporting equipment box configured to define boundary lines of the optically drawn, horizontal reaction area or reaction lines on a ground surface with a predetermined visible light band;
      a monochromatic light source on the same side of the vertical self-supporting equipment box for illuminating the optically drawn, horizontal reaction area as a whole or reaction lines with a wavelength that is outside the predetermined visible light band of the visible light pattern projector;
      a camera on the same side of the vertical self-supporting equipment box configured to function as a picture data detector for the optically drawn, horizontal reaction area at least at the wavelength of the monochromatic light source; and
      a data processing device configured to determine a ground contact and the reaction time of the person by utilizing picture data of the camera.

7. The vertical self-supporting equipment box according to claim 6, wherein the vertical self-supporting equipment box is configured to be utilized in T-test, static jump test, counter movement jump test, drop jump test, elasticity test, stiffness test or take-off reaction test.

8. The vertical self-supporting equipment box according to claim 6, wherein the vertical self-supporting equipment box is configured to be utilized in an acceleration or a speed test.

9. The vertical self-supporting equipment box according to claim 6, wherein the monochromatic light source is configured to illuminate the optically drawn, horizontal reaction area utilizing an infrared or visible wavelength.

10. The vertical self-supporting equipment box according to claim 6, wherein the at least two directional showing signal lights are configured to show to the person a next direction of movement inside the optically drawn, horizontal reaction area.

11. The vertical self-supporting equipment box according to claim 6, wherein the data processing device comprises:
   a processor;
   a memory including a computer program code;
the memory and the computer program code configured to, with the processor, cause the data processing device at least to:
   determine a time and a place of a body part of the person on the optically drawn, horizontal reaction area by utilizing picture data of the camera;

determine, from consecutive body part determinations, a movement data of the body part; and determine the ground contact and the reaction time by utilizing the determined movement data.

12. A method for measuring a ground contact and a reaction time of a person on an optically drawn, horizontal reaction area, wherein the method comprises following steps:

turning on a visible light pattern projector, a monochromatic light source and a camera;

the visible light pattern projector on a vertical side of the vertical self-supporting equipment box drawing boundary lines of the optically drawn, horizontal reaction area or reaction lines with a predetermined visible light band;

the monochromatic light source on the same side of the vertical self-supporting equipment box illuminating the optically drawn, horizontal reaction area as a whole or reaction lines with wavelength that is outside the predetermined visible light band of the visible light pattern projector;

a camera on the same side of the vertical self-supporting equipment box functioning as a picture data detector for the optically drawn, horizontal reaction area at least at the wavelength of the monochromatic light source;

determining a time and a place of a body part of the person on the optically drawn, horizontal reaction area by utilizing picture data of the camera;

determining, from consecutive body part determinations, a movement data of the body part;

determining the ground contact and the reaction time of the person by utilizing the determined movement data; and saving the ground contact and the reaction time measurement results to a memory of a data processing device and stopping the measurement session.

13. The method according to claim 12, wherein the method is one of the following: the ground contact time and the reaction time are determined in T-test, static jump test, counter movement jump test, drop jump test, stiffness test or take-off reaction test.

14. The method according to claim 12, wherein the method is one of the following: the ground contact time and the reaction time are determined in an acceleration or a speed test.

15. The method according to claim 12, wherein it further comprises sending the ground contact and the reaction time measurement results to a wireless communication device.

* * * * *